United States Patent [19]

Grisar et al.

[11] Patent Number: 5,146,294
[45] Date of Patent: Sep. 8, 1992

[54] PROCESS AND DEVICE FOR MEASURING ISOTOPE RATIOS

[75] Inventors: Roland Grisar, Freiburg; Wolfgang Riedel, Neuenburg, both of Fed. Rep. of Germany

[73] Assignee: Fraunhofer-Gesellschaft zur Forderung der angewandten Forschung e.V., Munich, Fed. Rep. of Germany

[21] Appl. No.: 678,118

[22] Filed: Apr. 1, 1991

[30] Foreign Application Priority Data

Apr. 19, 1990 [DE] Fed. Rep. of Germany ....... 4012454

[51] Int. Cl.$^5$ .......................................... G01N 21/35
[52] U.S. Cl. .................................. 356/435; 250/341; 250/343; 250/345; 356/246
[58] Field of Search ...................... 356/246, 440, 435; 250/576, 343, 345, 341

[56] References Cited

U.S. PATENT DOCUMENTS

| | | | |
|---|---|---|---|
| 3,218,914 | 11/1965 | Bartz et al. | 356/320 |
| 3,916,195 | 10/1975 | Burch et al. | 250/345 |
| 4,099,882 | 7/1978 | Hjalmar et al. | 356/246 X |
| 4,684,805 | 8/1987 | Lee et al. | 250/343 |

FOREIGN PATENT DOCUMENTS

370150A1  5/1990  European Pat. Off.
370151A1  5/1990  European Pat. Off.
3913481  11/1989  Fed. Rep. of Germany.

OTHER PUBLICATIONS

"Determination of Isotope Ratios, e.g., in Tracer work, by an Infrared Absorption Method," J. M. W. Milatz, J. C. Kluyver, J. Hardebol, The Journal of chemical Physics, vol. 19, No. 7, Jul. 1951, pp. 887-888.

"Automated Measurement of the Concentration and 13C Enrichment of Carbon Dioxide in Breath and Blood Samples Using the Finnigan MAT Breath Gas Analysis System", Charles M. Scrimgeour and Michael J. Rennie, Biomedical and Environmental Mass spectrometry, vol. 15, pp. 365-367 (1988).

"Comparison of Infrared and Mass-Spectrometric Measurements of Carbon-13/Carbon-12 Ratios", William W. Wong, Int. J. Appl. Radiat. Isot., vol. 36, No. 12, pp. 997-999 (1985).

"Tracers in Metabolic Research—Radioisotope and Stable Isotope/Mass Spectrometry Methods", Robert R. Wolfe (1984) pp. 198-205.

"High Resolution Infrared Diode Laser Spectroscopy for Isotope Analysis—Measurement of Isotopic Carbon Monoxide", Peter S. Lee and Richard F. Majkowski, Appl. Phys. Lett. 48(10), (1986). pp. 619-621.

"Measurement of D20 Concentrations at Tracer Levels in Small Samples Obtained from Paediatric Patients", Ch. Fusch and H. Moeller J. Clin. Chem. Clin. Biochem, vol. 26, pp. 715-721 (1988).

*Primary Examiner*—Vincent P. McGraw
*Attorney, Agent, or Firm*—Baker & Daniels

[57] ABSTRACT

A process and device for measuring the isotope ratio, specifically of stable isotopes, of chemical substances in a gas to be examined, the process including alternately charging a sample cell with a reference gas and a measuring gas containing the gas to be examined; adding a metrologically neutral gas to the gas to be examined; varying the mixing ratio of this measuring gas by changing the share of neutral gas being added; and calculation of the isotope ratio $V_p$ of the substance according to the equation:

$$V_P = V_R \cdot \left(1 + \frac{M_2 - R_2}{R_2}\right) \cdot \left(1 + \frac{M_1 - R_1}{R_1}\right)^{-1}.$$

The device includes a White cell having mirrors on each end of the longitudinal length of the cell, a pair of first beam openings located on a longitudinal end, a pair of second beam openings in spaced parallelism on the longitudinal sides of the White cell and a gas inlet and gas outlet located near each mirror.

13 Claims, 3 Drawing Sheets

PROCESS AND DEVICE FOR MEASURING ISOTOPE RATIOS

BACKGROUND OF THE INVENTION

The invention concerns a process for measuring the isotope ratio, specifically of stable isotopes of chemical substances in a gas to be examined, the process featuring the following steps:

charging a sample cell alternately with a reference gas, and a measuring gas containing the gas to be examined; and determining the content of isotopes of the substance in the alternately available gases;

and concerns a device for the application of the process.

Such a process is known from chapter 16 of the book titled "Tracers in Metabolic Research—Radioisotopes and Stable Isotope/Mass Spectrometry Methods" by Robert R. Wolfe, Alan R. Liss Inc., N.Y. (1984). A reference gas is on hand in a reference gas cell and a measuring gas in a measuring gas cell. The pressure in these two cells is adapted to one another via a vacuum line that connects them and leads to a pump. A molecular gas flow is passed through a capillary line from each of the cells to a switching valve, the outlet of which latter leads to a mass spectrometer in which the isotopes, due to their different masses, are differently accelerated and spatially separated on different detectors.

Using the mass spectrometer, the measuring gas and the reference gas are in a time sequence cyclically analyzed in succession. This makes it possible to enhance the accuracy of the measurement because all of the test conditions of the mass spectrometer, such as the condition of the source, of the analyzer means etc., can be held constant while the measurement with the measuring gas and the reference gas is conducted.

The greater the number of cyclic measurements performed and the shorter the time spacing between changeovers is selected, the better will be the accuracy of the isotope ratio determined. Therefore, the disadvantage associated with the process is that in the case of longer periods between the changeovers, same test conditions of the following isotope analyzer means cannot be guaranteed.

This is particularly advantageous when using the known process for the infrared-spectroscopic determination of the isotope ratio, since fluctuations of the test conditions, such as the frequency and intensity constancy of the laser, for instance due to the temperature of the laser diode chip, may occur also within short time periods.

From "High resolution infrared diode laser spectroscopy for isotope analysis—Measurement of isotopic carbon monoxide" from Appl. Phys. Lett. 48, page 619 (1986) there is known to determine the isotope ratio of stable isotopes with the use of a tunable infrared diode laser. The prior system uses a temperature-stabilized lead salt diode laser and a two-part sample cell, each with a predetermined light path through the differently long sections of the sample cell.

Usually, the gaseous substance of interest is primarily available in a predetermined natural isotope composition, which in addition to a major isotope features traces of other isotopes whose concentration frequently is lower by a factor in the order of 100. Therefore, the long light path serves to amplify the extinction of the lesser occurring isotope, in order to balance the relative strength of the extinctions of the individual isotopes among one another and to utilize in a similar fashion the measuring sensitivity of the detectors.

The lead salt diode laser impinges alternately on the long and the short arm of the sample cell containing the measuring gas. By shifting the sample cell, the laser beam traverses either the short or the long arm of the sample cell and impinges on a detector. The concentration of the individual isotopes can be calculated from the respective extinction of the laser beam, with the aid of Lambert-Beer's law. The relative error of the isotope distribution so measured is stated to be 2.5 per mill in the prior art and, thus, is by a factor of 25 greater than the corresponding error in the mass spectrometric measurement.

Based on this prior art, the invention has as its underlying problem of providing a process which with a reduced cyclic measuring time features a greater accuracy in determining the relative isotope ratio.

SUMMARY OF THE INVENTION

This problem is inventionally solved for a process of the initially mentioned type in that the following additional process steps are included:

addition of a metrologically neutral gas to the gas to be examined, thereby generating a measuring gas by mixing these two gases, varying the mixing ratio of the measuring gas by changing the share of the joining inert gas in such a way that the determined content of the substance of the one isotope 1 in the reference gas $R_1$ and in the measuring gas $M_1$ is essentially equal, and calculating the isotope ratio $V_P$ of the substance from the content of the substance on the other isotope 2, measured in timewise alternation, in the reference gas $R_2$ and in the measuring gas $M_2$, under inclusion of the known isotope ratio $V_R$ of the reference gas according to the equation:

$$V_P = V_R \cdot \left(1 + \frac{M_2 - R_2}{R_2}\right) \cdot \left(1 + \frac{M_1 - R_1}{R_1}\right)^{-1}.$$

Due to the fact that the measuring gas is diluted by a metrologically neutral gas during the measurement, the concentrations of isotope 1 in the reference gas and in the measuring gas can be mutually approximated by recursive definition. Isotope 1 is preferably the one occurring at a higher concentration than isotope 2 of the substance to be analyzed in the gas.

After a certain time duration of this process step, an approximate equality of the isotope concentrations of isotope 1 in the reference gas and in the measuring gas has been established. Next, in addition to a constant monitoring of the equality of these concentrations of isotope 1 in the reference gas and in the measuring gas, the concentrations of isotope 2 in the reference gas and in the measuring gas are determined and the wanted isotope ratio is calculated according to the equation given above from the known isotope ratio of the reference gas.

This makes it possible to determine more accurately and within a shorter time period the relative isotope ratio with regard to the isotope ratio of the reference gas.

In a preferable embodiment of the invention, the process is utilized in conjunction with an infrared laser spectrometer. Such a spectrometer offers the advantage of being considerably smaller than a mass spectrometer and, therefore, is able to be rolled, e.g., to the bed of a patient in a simple manner, so that the patient or a sample of the patient's respiratory gas need not be brought to the unwieldy mass spectrometer analysis apparatus. Used as sample cell is a White cell where a laser beam is split and the two resulting light beams traverse the cell essentially at a right angle to each other. The one laser beam traverses the White cell folded, e.g., 8 or 16 times, while the other laser beam passes through the White cell at a right angle to the folded laser beam. In a compact cell of $8 \times 2 \times 1$ centimeters it is thus possible with 16 passes of the folded laser beam to achieve a travel difference of the light paths in the sample cell of nearly 100. This makes it possible, for instance in the case of $CO_2$, to adapt the very different isotope concentrations of $^{12}CO_2$ and $^{13}CO_2$ at preselected lines to one another in their extinction effect and to determine them infrared-spectrometrically at high accuracy.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
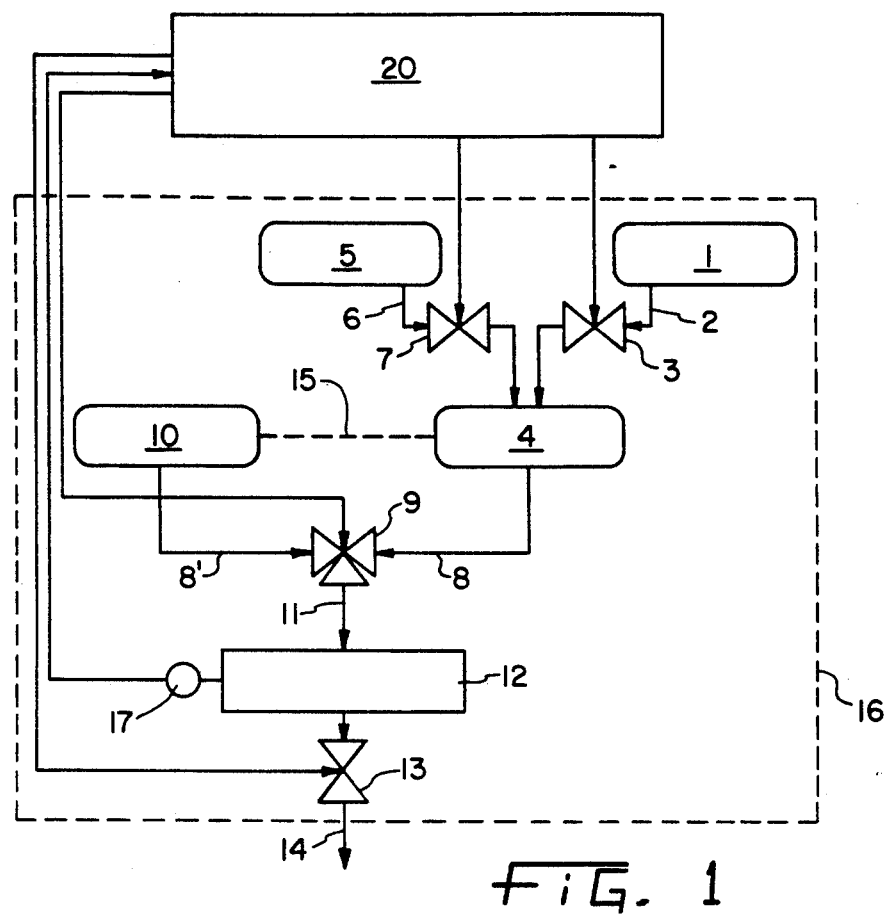
FIG. 1 shows a device for the application of the measuring process.

Corresponding reference characters indicate corresponding parts throughout the several views. The exemplifications set out herein illustrate a preferred embodiment of the invention, in one form thereof, and such exemplifications are not to be construed as limiting the scope of the invention in any manner.

DESCRIPTION OF THE PREFERRED EMBODIMENT

FIG. 1 shows a block diagram covering the application of the process for determination of isotope ratios on the example of $CO_2$. Naturally, it is also possible to analyze the isotope ratios of other gaseous substances, for instance of $SO_2$, NO or CO. The process can be applied both in a mass-spectrometric and an infrared-spectrometric examination.

The illustration depicted in FIG. 1 serves to check the degree of $^{13}CO_2$ enrichment in the respiratory gas of a patient. The patient fills a respiratory gas supply container 1 with his exhaled respiratory gas, which via a line 2 and a first dosing valve 3 is passed into a respiratory gas intermediate container 4.

A metrologically neutral gas, for instance nitrogen or synthetic air, is stored in a supply container 5. The metrologically neutral nitrogen can be introduced in the respiratory gas within container 4 by way of a feedline 6 and a second dosing valve 7.

The respiratory gas within container 4 connects by way of a measuring gas line 8 with a T-shaped changeover valve 9. A reference gas container 10 is connected to the other entrance of the changeover valve 9 by way of a reference gas line 8'. The changeover valve 9 passes either the gas mixture of respiratory gas and metrologically neutral gas temporarily stored in the respiratory gas intermediate container 4 or the reference gas stored in the reference gas container 10 via a feedline 11 into a double sample cell 12. Upon passage of either of the gas mixture or neutral gas from cell 12, the gas is passed through a reduction valve 13 to a dissipating pump 14. In a mass-spectrometric process, the double sample cell 12 is substituted by the ionizing chamber of the mass spectrometer.

The dash-dot line 15 indicates a pressure equalization means between the reference gas container 10 and the respiratory gas intermediate container 4. This means that intermediate volumes of the containers 4 and 10 are sucked off by a pump, which is not illustrated in the drawing, so that the gas in lines 8 and 8' which flows to the changeover valve 9 will always have the same pressure.

The entirety of the containers 1, 4, 5, and 10, the valves 3 and 7 as well as the double sample cell 12 are controlled to a constant temperature. This is indicated by the dash-dot rectangle of an isolation container 16. A suitable control temperature, e.g., is 40° C., which is maintained at an accuracy of, e.g., $\frac{1}{4}$° C.

The dosing valves 3 and 7, the changeover valve 9 as well as the flow control valve 13 are connected to an evaluation and control unit via control lines.

The pressure of the gas currently contained in the double sample cell 12 ranges preferably between 1 and 100 millibars, and in the described embodiment at approximately 50 millibars. A pressure gauge 17 senses the inside pressure of the sample cell 12, and its output signal proceeds to the evaluation and control unit 20.

Figure 2:
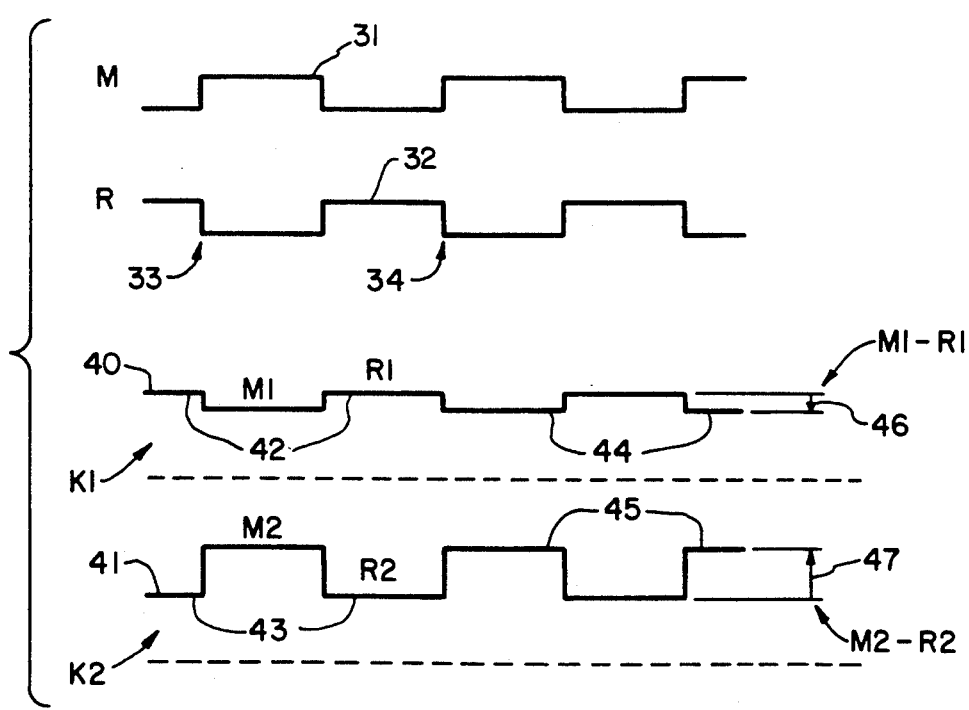
FIG. 2 is an illustration of measuring signals in time resolution.
Figure 3:
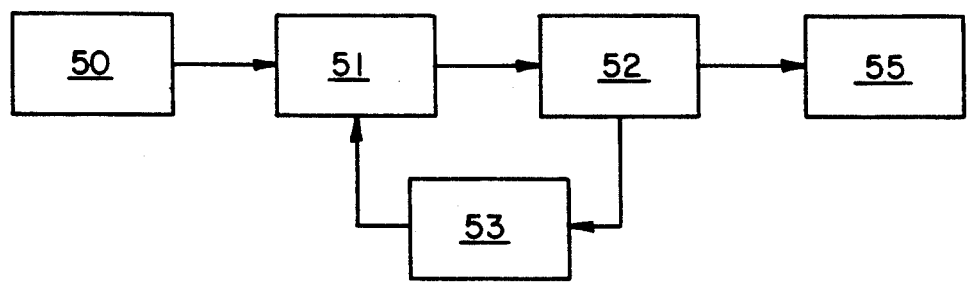
FIG. 3 is a block diagram of the measuring preparation.

The measuring principle of the process is illustrated in FIGS. 2 and 3, with FIG. 2 showing the time sequences of measuring and control signals, while FIG. 3 represents a flow chart of the measuring preparation and the measurement.

The curves 31 and 32 in FIG. 2 show the time progression of the position of the changeover valve 9. At the point in time 33, the changeover valve 9 switches according to curve 31 for its measuring gas side M with the feedline 8 from "closed" to "open", while the curve 32 shows the closing of the feedline 8' of the reference gas branch R of the changeover valve 9. Given by the time spacing of the periodically repeating points in time 34 and 33, the frequency of change may in the case of the infrared spectrometer described hereafter amount to several Hertz, making a close succession of different measuring conditions possible.

The curves 40 and 41 show the signals of the measuring channels of the $^{12}CO_2$ and of the $^{13}CO_2$ in the respiratory gas of a patient, which occurs at a by far lower concentration. Illustrated in sections 42 and 43 is the respective $^{12}CO_2$ and $^{13}CO_2$ concentration in the reference gas, while in the areas 44 and 45 the respective ranges in the measuring gas are illustrated. The time contingency of the measuring signals is a direct consequence of the changeover of the changeover valve 9 between the feedline of the reference gas 8' and that of the respiratory mixed gas 8.

As evidenced clearly by FIG. 2, the concentration of $^{12}CO_2$ in the reference gas is higher than in the measuring gas, whereas the concentration of $^{13}CO_2$ in the measuring gas is higher than in the reference gas. However, the absolute scale, and with it the height of the signals of the steps in the two channels, is thus selected arbitrarily.

A step 46 results between the concentrations of $^{12}CO_2$ in the reference gas R and in the measuring gas M, and a step 47 that differs from the respective concentrations of $^{13}CO_2$.

FIG. 3 shows a flow chart illustrating the application of the process. At the start of the process, pure respiratory gas is passed from the respiratory gas container 1 via the respiratory gas intermediate container 4, alternating with the reference gas, from the container 10 through the changeover valve 9 into the double sample cell 12. This is denoted in the flow chart by the initial step 50. Next, the amount of respiratory gas from the container 1 is reduced by means of dosing valves 3 and 7, while the amount of neutral measuring gas, for instance nitrogen, from the container 5 is increased. This control step is indicated by the box 51. Evaluated as an output signal of the double measuring cell 12 are only the concentrations of the $^{12}CO_2$ channel; that is, the curve 40 or its values 42 and 44. Should the height of step 46, which represents the concentration difference between the measuring and the reference gas $^{12}CO_2$ divided by the concentration of $CO_2$ in the reference gas, be greater than, e.g., one hundredth or five one thousandths, the opening state of the dosing valves 3 and 7 is changed further in a controller 53, causing the admixture of additional nitrogen or less nitrogen to the respiratory gas in the respiratory gas intermediate container 4, which corresponds to a further control step of the box 51.

If then at one point in time, in the control circuit 52, the condition is met such that the difference of the concentrations is less than one hundredth of the respective concentration of the reference gas, the measuring module 55 is accessed in which, according to the equation $$V_P = V_R \cdot \left(1 + \frac{M_2 - R_2}{R_2}\right) \cdot \left(1 + \frac{M_1 - R_1}{R_1}\right)^{-1},$$

the concentration ratio of the measuring gas $V_P$ is computed from the known concentration ratio of the reference gas $V_R$. $R_1$ and $R_2$ with reference numerals 42 and 43, respectively, signify the content of the substance in the isotope 1 or 2 in the reference gas, while $M_1$ and $M_2$ with reference numerals 44 and 45, respectively, of the signal values indicate the share of isotope 1 or 2 in the measuring gas. Realized thereby is sort of a null method in which the one, preferably high isotope concentration of the measuring gas and of the reference gas can be adapted to one another and the slight isotope concentration can be determined with great sensitivity.

Figure 4:
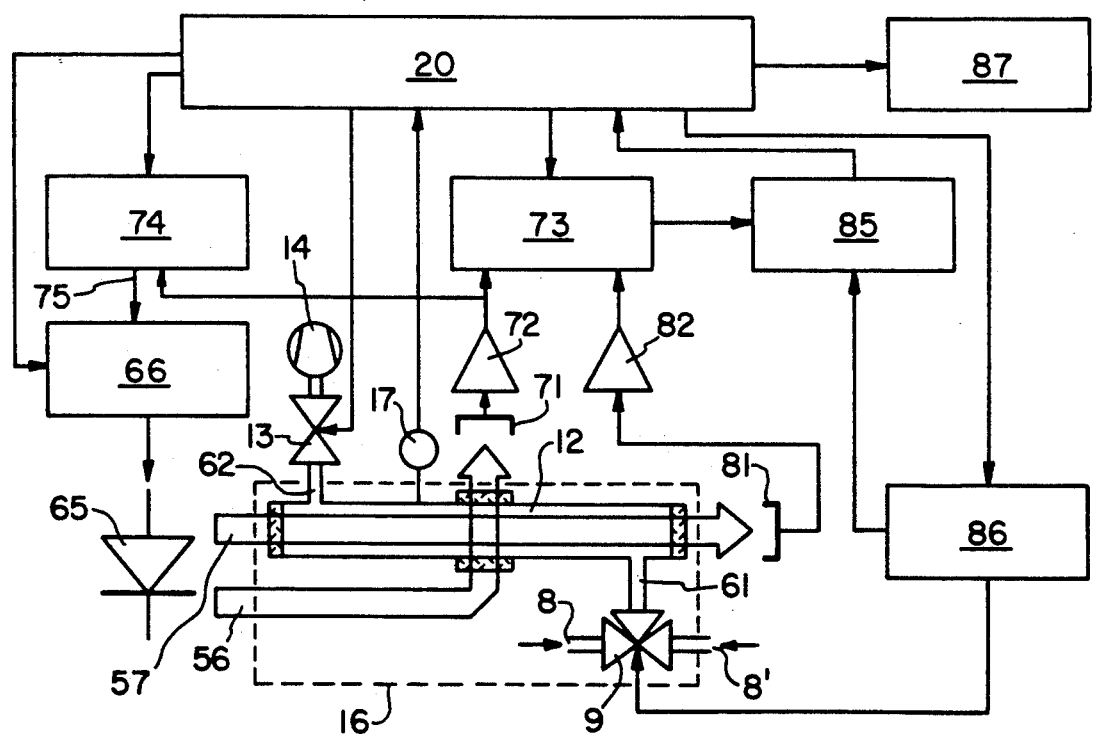
FIG. 4 is a schematic view of an infrared laser spectrometer for the application of the process.

FIG. 4 shows the optical and electronic structure of an infrared laser spectrometer used with a vacuum structure according to FIG. 1. Connected to the changeover valve 9 shown in FIG. 1 is the double sample cell 12 which in a favorable embodiment is a White cell. The gas flowing from the changeover valve 9 is introduced into the White cell at its end 61 and passes out of it at its other end 62, via the flow control valve 13 to the pump 14, so that the gas stemming from the changeover valve 9 will flow through the entire White cell 12 and drive out any gases previously contained in it.

Controlled to a constant temperature by a temperature control not shown in the figure, a diode laser 65 is activated by a laser power supply 66 which by way of a control line is connected with a control and evaluation unit 20. The temperature control maintains the temperature, e.g., near the temperature of the isolation container 16, for instance at 40° C.

The laser diode 65 preferably receives rectangular pulses in a pulsed operation. Deriving thereof is a slowly increasing frequency of the generated laser beam during the pulse width, so that two adjacent absorption lines of the $^{12}CO_2$ and the $^{13}CO_2$ can be swept at the frequency. The frequency swing amounts to, e.g., 0.4 cm$^{-1}$. The laser frequency is preferably selected so that the absorption strengths of the respective absorption lines of $^{12}CO_2$ and $^{13}CO_2$ will at changing temperature undergo a similar or like change. Achieved thereby is that preferably one line pair is selected where $^{12}CO_2$ and $^{13}CO_2$ have the same rotational quantum number in the P- or R-branch of the same vibratory transition.

In $CO_2$, which is the same as in many other gases to be examined, one isotope component, $^{12}CO_2$, occurs in nature considerably more frequently than the other isotope component, $^{13}CO_2$, which is used, e.g., for tagging. To obtain similar, well evaluable extinction strengths it is therefore necessary for the measuring path of the weakly occurring isotope to be considerably longer than the measuring path of the other isotope.

Therefore, the light stemming from the laser diode 65 is split in two beams 56 and 57, of which the one beam 56 passes transversely through the White cell 12 and impinges on a first detector 71 for the $^{12}CO_2$, the output signal of which is passed via an amplifier 72 to an integral evaluation circuit 73 and the frequency stabilization 74, while the laser beam 57 pertaining to the $^{13}CO_2$, folded several times, passes through the White cell 12 and falls on a second detector 81 whose output signal is via an amplifier 82 transmitted as well to the integral evaluation 73.

The absorption signal pertaining to the $^{12}CO_2$, which from the time frequency-dependent overall absorption signal can be filtered out, for instance by a time control, serves by way of the frequency stabilization 74 to stabilize the laser diode 65, by generating with it a control signal 75 which activates the laser power supply 66. This laser diode control derives, e.g., from the German patent document 37 34 401.

In the integral evaluation 73 there are created, from the overall absorption signal of each individual absorption line, the signals 40 and 41 illustrated in FIG. 2, which are proportional to the concentration. They are transmitted to a two-channel lock-in amplifier 85 which, on the other hand, receives a signal from the measurement sequence control 86 containing the information on the gas presently contained in the sample cell 12. The two-channel lock-in amplifier is connected with the control and evaluation unit 20 and the measuring value output 87.

The control and evaluation unit 20 periodically transmits a control signal to the measurement sequence control 86, which consequently causes the changeover valve 9 to switch. At the same time, the laser power supply 66 and the frequency stabilization 74 are activated at a higher frequency, for instance of 1 kilohertz, causing the laser to pulsewise ramp up to a frequency that sweeps the frequency range of the two absorption maxima of the $^{12}CO_2$ and the $^{13}CO_2$ that is of interest, without any frequency jump.

Figure 5:
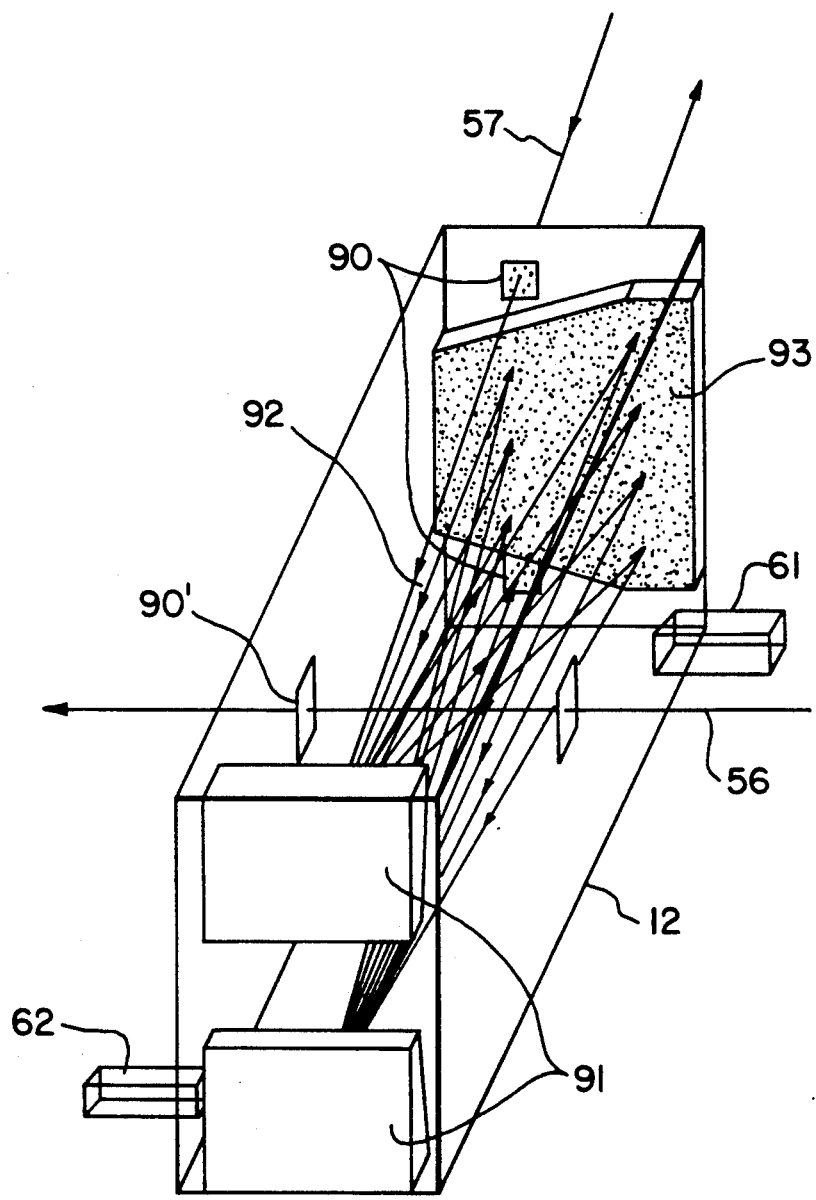
FIG. 5 is a White cell for use as sample cell according to FIGS. 1 and 4.

FIG. 5 shows in a perspective view a White cell 12, which in FIG. 4 is indicated only schematically. The input beam 57 of the $^{13}CO_2$ proceeds through a window opening 90 into the White cell 12 and is reflected by the split end mirror 91. The beam 92 reflected by the end mirror 91 is by the mirror 93, arranged on the side of said window opening 90, reflected back again to the split mirror 91, so that the beam will after 8 or 16 passes through the White cell 12 leave the White cell 12 through another window opening 90. Featuring a long path through the absorbing gas, this beam serves to determine the extinction of the weakly occurring isotope.

At a right angle to it, the laser beam 56 proceeds through the volume of the White cell 12, scanning the extinction curve pertaining to the $^{12}CO_2$. Arranged on the White cell 12, in the vicinity of the mirrors 91 and 93, are the gas inlet and gas outlet openings 61 and 62, preferably on opposite corners of the White cell 12 block.

Having a length of 6 centimeters, a width of 1 centimeter and a height of 2 centimeters, the White cell can be filled with measuring gas M or reference gas R with the aid of the changeover switch 9, at a clock frequency in the order of 10 Hertz, guaranteeing equal test conditions for both measuring branches.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A process for measuring the isotope ratio, specifically of stable isotopes, of chemical substances in a gas to be examined, the process featuring the following steps:

alternately charging a sample cell with a reference gas and a measuring gas containing the gas to be examined, and determining the isotope content of the substance contained in the alternately present gases, characterized by the following further process steps:

addition of a metrologically neutral gas to the gas to be examined, generating a measuring gas by mixing these two gases;

variation of the mixing ratio of the measuring gas by changing the share of neutral gas to be added, in such a way that the determined contents of the substance of the one isotope 1 in the reference gas $R_1$ and in the measuring gas $M_1$ are essentially equal; and computation of the isotope ratio $V_P$ of the substance from the alternately determined content of the substance on the other isotope 2 in the reference gas $R_2$ and in the measuring gas $M_2$, under inclusion of the known isotope ratio $V_R$ of the reference gas according to the equation:

$$V_P = V_R \cdot \left(1 + \frac{M_2 - R_2}{R_2}\right) \cdot \left(1 + \frac{M_1 - R_1}{R_1}\right)^{-1}.$$

2. The process according to claim 1, wherein the isotope 1 is the isotope occurring at a higher concentration.

3. The process according to claim 1, wherein the determined contents of the substance in the one isotope 1 in the reference gas $R_1$ and in the measuring gas $M_1$ are essentially equal, if $(M_1 - R_1)/R_1$ is smaller than 0.01.

4. The process according to claim 1, wherein the metrologically neutral gas is nitrogen or synthetic air.

5. The process according to claim 1, wherein the sample cell is transilluminated using a first light beam whose extinction is determined on an absorption line of the isotope 1, and using a second light beam whose extinction is determined on an absorption line of the isotope 2, independently from each other, thereby obtaining the isotope content according to Lambert-Beer's law.

6. The process according to claim 5, wherein a laser beam of a given wavelength is used where the substance to be examined features two closely adjacent extinction lines in a laboratory transition for two similar rotational transition quantum numbers of the two isotopes.

7. The process according to claim 6, wherein the transition of the one isotope is located in the P-branch and the transition of the other isotope in the R-branch.

8. The process according to claim 2, wherein the determined contents of the substance in the one isotope 1 in the reference gas $R_1$ and in the measuring gas $M_1$ are essentially equal, if $(M_1 - R_1)/R_1$ is smaller than 0.01.

9. The process according to claim 2, wherein the metrologically neutral gas is nitrogen or synthetic air.

10. The process according to claim 3, wherein the metrologically neutral gas is nitrogen or synthetic air.

11. The process according to claim 2, wherein the sample cell is transilluminated using a first light beam whose extinction is determined on an absorption line of the isotope 1, and using a second light beam whose extinction is determined on an absorption line of the isotope 2, independently from each other, thereby obtaining the isotope content according to Lambert-Beer's law.

12. The process according to claim 3, wherein the sample cell is transilluminated using a first light beam whose extinction is determined on an absorption line of the isotope 1, and using a second light beam whose extinction is determined on an absorption line of the isotope 2, independently from each other, thereby obtaining the isotope content according to Lambert-Beer's law.

13. The process according to claim 4, wherein the sample cell is transilluminated using a first light beam whose extinction is determined on an absorption line of the isotope 1, and using a second light beam whose extinction is determined on an absorption line of the isotope 2, independently from each other, thereby obtaining the isotope content according to Lambert-Beer's law.

* * * * *